United States Patent [19]

Dobson et al.

[11] Patent Number: 4,849,428
[45] Date of Patent: Jul. 18, 1989

[54] CYCLIC ANTI-INFLAMMATORY DERIVATIVES OF DI-TERT-BUTYLPHENOL COMPOUNDS, COMPOSITIONS AND USE

[75] Inventors: Roy L. M. Dobson, Fairfield; Maurice E. Loomans; Randall S. Matthews, both of Cincinnati, all of Ohio; Joseph A. Miller, Baton Rouge, La.

[73] Assignee: The Procter & Gamble Company, Cincinnati, Ohio

[21] Appl. No.: 123,756

[22] Filed: Nov. 23, 1987

[51] Int. Cl.$^4$ ............... A61K 31/34; A61K 31/365; C07D 307/79; C07D 307/83
[52] U.S. Cl. ........................... 549/307; 549/466; 549/462; 549/14; 549/22; 549/370; 549/30; 549/39; 549/448
[58] Field of Search ............. 549/466, 462, 307, 14, 549/22, 370, 30, 39, 448; 514/469, 470, 467, 440, 439, 452, 436, 433

[56] References Cited

U.S. PATENT DOCUMENTS

| | | | |
|---|---|---|---|
| 3,717,611 | 2/1973 | Baumer et al. | 260/45.95 G |
| 3,829,446 | 8/1974 | Kadin | 549/307 |
| 3,862,133 | 1/1975 | Layer | 260/343.3 |
| 4,130,666 | 12/1978 | Moore | 424/331 |
| 4,298,615 | 11/1981 | Gerd-Ulrich et al. | 549/462 |
| 4,325,863 | 4/1982 | Hinsken et al. | 624/111 |
| 4,431,656 | 2/1984 | Katsumi et al. | 424/273 R |
| 4,440,784 | 4/1984 | Katsumi et al. | 424/308 |
| 4,514,415 | 4/1985 | Weak | 514/470 |
| 4,708,966 | 11/1984 | Loomans et al. | 514/689 |
| 4,711,903 | 12/1987 | Mueller et al. | 514/381 |

FOREIGN PATENT DOCUMENTS

| | | | |
|---|---|---|---|
| 2608697 | 9/1976 | Fed. Rep. of Germany | 549/307 |
| 60-54315 | 3/1985 | Japan . | |
| 61-218571 | 3/1985 | Japan . | |

OTHER PUBLICATIONS

Swingle, Bell & Moore, "Anti-Inflammatory Activity of Antioxidants", Chapter 4 of Anti-Inflammatory and Anti-Rheumatic Drugs, vol. III, Rainsford (ed.), CRC Press, Inc., Boca Raton, Fla., 1985, pp. 105–126.
Soviet Inventions Illustrated, Week 8429, SU 1054-34-2-A, Derwent Publications, Ltd., London, England (1984).
Magnusson, "Reactions Between Quinones and Carbonyl Compounds Catalyzed by Aluminum Oxide", Acta Chemica Scandinavica, vol. 18, No. 2 (1964), pp. 421–432.
Layer, "Synthesis of 2(3H)Benzofuranones from Glyoxal and Phenols", Journal of Heterocyclic Chemistry, vol. 12, No. 5 (1975), pp. 1067–1068.
Hauff, Krauss & Rieker, "Spin Density Distribution in Free Radicals, VII, Participation of the Carbon–Carbon Bond in the Mesomerism of Phenoxy Radicals", Chem. Ber., vol. 105, No. 4 (1972), pp. 1446–1455.
Gavrilov, Meshcheryakov, Kalyagina, Dobronravova & Vereshchagin, "Synthesis of Diarylpropynones and their Antibiotic Activity", Khimiko-Farmatsevticheskii, Zhurnal, vol. 12, No. 9 (Sep. 1978), pp. 42–56.

Primary Examiner—Mary C. Lee
Assistant Examiner—John A. H. Russell
Attorney, Agent, or Firm—Milton B. Graff, IV; Jack D. Schaeffer; Richard C. Witte

[57] ABSTRACT

The present invention involves compounds having the structure:

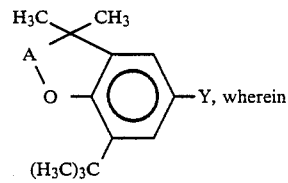

(a) —A— is selected from the group consisting of

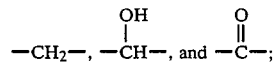

(b) —Y is selected from certain low molecular weight moieties which terminate in specific functional groups: —C≡CH,

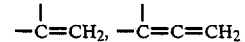

and aldehydes in the form of their acetals;
pharmaceutical compositions comprising such compounds; and methods for treating inflammation by administering such compounds.

19 Claims, No Drawings

CYCLIC ANTI-INFLAMMATORY DERIVATIVES OF DI-TERT-BUTYLPHENOL COMPOUNDS, COMPOSITIONS AND USE

BACKGROUND OF THE INVENTION

The present invention relates to novel specifically-substituted derivatives of di-tert-butylphenol compounds, which are effective as anti-inflammatory, analgesic and/or antipyretic agents. The present invention further relates to pharmaceutical compositions which are useful for treating diseases which involve inflammation, pain, and/or fever. Finally, the present invention relates to methods for treating diseases characterized by inflammation.

The search for new non-steroidal anti-inflammatory ("NSAI") drugs over the last 10 to 20 years has led to the testing by various researchers and companies of thousands of compounds for efficacy as anti-inflammatories. The search has raised many questions, but provided few answers, about how and why some compounds are efficacious and others are not, especially for substituted di-tert-butylphenol compounds. This search, and the results and questions raised thereby, are discussed more fully in "Anti-inflammatory Activity of Anti-oxidants", by K. F. Swingle, et al., Chapter 4 of *Anti-inflammatory and Anti-rheumatic Drugs*, Vol. III (K. D. Rainsford, Editor; C R C Press, Inc.; 1985), pages 105-126, which is incorporated herein by reference.

Notwithstanding the great effort already put forth to identify NSAI drugs, there remains a continuing need to identify new compounds and compositions which are effective for treating inflammation and inflammatory diseases such as rheumatoid arthritis and osteoarthritis. It is accordingly an object of the present invention to provide compounds which are effective anti-inflammatory agents, as well as pharmaceutical compositions containing these compounds. It is a further object of the present invention to provide methods for treating diseases characterized by inflammation.

It is a further object of the present invention to provide compounds which have one or more of the following uses: anti-inflammatory agents, analgesic agents, antipyretic agents, antiarthritic agents, bone modifying agents, immunomodulating agents, antilipidemic agents, antiresorptive agents, or agents for reversing ischaemia-induced cell damage; and pharmaceutical compositions containing these compounds. A still further object of the present invention is to provide compounds, and compositions containing these compounds, which have high efficacy, low toxicity (such as low gastrointestinal irritability), prolonged duration of action, and/or good therapeutic indices.

These and other objects will become readily apparent from the detailed description which follows.

SUMMARY OF THE INVENTION

The present invention relates to specifically-substituted cyclic derivatives of 2,6-di-tert-butylphenol compounds, which are effective as one or more of the following: anti-inflammatory agents, analgesic agents, antipyretic agents, antioxidant agents, antiarthritic agents, immunomodulating agents, antilipidemic agents, antiresorptive agents, or agents for reversing ischaemia-induced cell damage. These phenyl compounds are substituted in the 4-position with a low molecular weight moiety which terminates in a specific functional group. These functionalities are —C≡CH, $$-\overset{|}{C}=CH_2, \quad -\overset{|}{C}=C=CH_2,$$

and aldehydes in the form of their acetals.

The present invention further relates to pharmaceutical compositions. These compositions comprise a compound of the present invention and a pharmaceutically-acceptable carrier.

Finally, the present invention also relates to methods for treating diseases characterized by inflammation, such as rheumatoid arthritis and osteoarthritis, in humans or lower animals. Such methods comprise administering to a human or lower animal in need of such treatment a safe and effective amount of a compound or composition of the present invention.

DETAILED DESCRIPTION OF THE INVENTION

Anti-inflammatory Agents

The compounds useful in the present invention are specifically-substituted cyclic derivatives of 2,6-di-tert-butylphenol compounds, which are substituted in the 4-position with a specific low-molecular-weight moiety which terminates in a specific functional group. The terminal functionality is selected from —C≡CH, $$-\overset{|}{C}=CH_2, \quad -\overset{|}{C}=C=CH_2,$$

or aldehydes in the form of their acetals. Preferred are the —C≡CH and acetal terminal functionalities.

Specifically, the compounds of the present invention have the general structure:

In this structure, —A— is selected from the group consisting of $$-CH_2-, \quad -\overset{OH}{\underset{|}{CH}}-, \quad \text{and} \quad -\overset{O}{\underset{\|}{C}}-.$$

Preferred —A— is —CH₂— or $$-\overset{O}{\underset{\|}{C}}-,$$

and most preferred —A— is —CH₂—.

—Y is selected from the group consisting of:

1. —(CR¹₂)ₙ—C≡C—H, wherein n is an integer from 1 to about 6;
2.

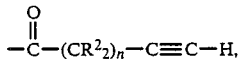

wherein n is an integer from 0 to about 5;

3.

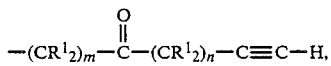

wherein m is an integer from 1 to about 5, and m+n is an integer from 1 to about 5; preferred is m=2;

4.

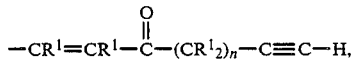

wherein n is 0 or 1;

5. $-(CR^1{}_2)_n-CR^3=CH_2$, wherein n is an integer from about 2 to about 6;

6.

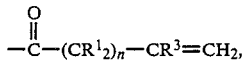

wherein n is an integer from 0 to about 5;

7.

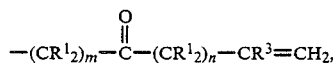

wherein m is an integer from 1 to about 3, and m+n is an integer from 1 to about 3; preferred is m=2;

8.

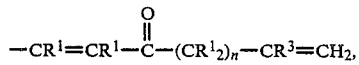

wherein n is an integer from 0 to about 3;

9. $-(CR^1{}_2)_n-CR^3=C=CH_2$, wherein n is an integer from 0 to about 6;

10.

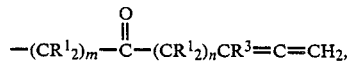

wherein m+n is an integer from 0 to about 5; preferred is m=0 or 2;

11.

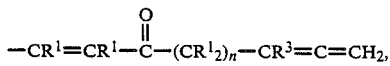

wherein n is an integer from 0 to about 3;

12. $-(CR^1{}_2)_n-CH(ZR^4)_2$, wherein n is an integer from 1 to about 6; and

13.

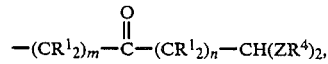

wherein n is an integer from 1 to about 5, m is an integer from 0 to about 4, and m+n is an integer from about 1 to about 5; preferred is m=0 or 2.

In these substituent —Y groups, each —$R^1$ is independently selected from the group consisting of —H, —$OR^3$, —$NR^3{}_2$, —$NR^3{}_3{}^+$, —$N(R^3)C(O)R^3$, —$O_2CR^3$, —$CO_2R^3$, —$C(O)NR^3{}_2$, straight or branched chain saturated alkyl group having from 1 to 3 carbon atoms, and straight or branched chain unsaturated alkyl group having from 1 to about 3 carbon atoms, or two —$R^1$'s on the same carbon atom are =O or =$CR^3{}_2$. Preferably, —$R^1$ is —H, —OH, methyl, or ethyl, or two —$R^1$'s on the same carbon atom are =O or =$CH_2$, and further preferred is no more than about two —$R^1$ groups being other than —H. Most preferred is all —$R^1$ groups being —H.

Each —$R^2$ is independently selected from the group consisting of —H, —$OR^3$, —$NR^3{}_2$, —$NR^3{}_3{}^+$, —$N(R^3)C(O)R^3$, —$O_2CR^3$, —$CO_2R^3$, —$C(O)NR^3{}_2$, straight or branched chain saturated alkyl group having from 1 to about 3 carbon atoms, and straight or branched chain unsaturated alkyl group having from 1 to about 2 carbon atoms, or two —$R^2$'s on the same carbon atom are =O or =$CR^3{}_2$. Preferably, —$R^2$ is —H, —OH, methyl, or ethyl, or two —$R^2$'s on the same carbon atom are =O or =$CH_2$, and further preferred is no more than about two —$R^2$ groups being other than —H. Most preferred is all —$R^2$ groups being —H.

Each —$R^3$ is independently selected from the group consisting of —H, methyl and ethyl. Preferably —$R^3$ is —H.

Each —$R^4$ is independently selected from the group consisting of —$CH_3$ and —$CH_2CH_3$, or the —$R^4$'s may be joined to form a cyclic acetal such that both —$R^4$'s together are one group selected from —$(CH_2)_2$— and —$(CH_2)_3$—. Preferred is both —$R^4$ groups being methyl, or both —$R^4$ groups together being —$CH_2CH_2$—. Most preferred is both —$R^4$ groups being methyl.

Each —Z— is independently selected from the group consisting of —O—, —S—, —NH—, and —$NR^4$—. Preferred is —Z— being —O— or —S—, and most preferred is both —Z— groups being the same atom selected from —O— or —S—.

Specifically preferred acetal groups (i.e., —$CH(ZR^4)_2$ groups) are

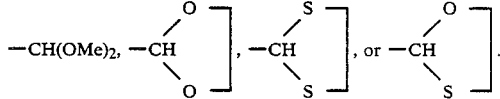

Most preferred specific acetals are

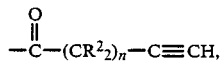

and, especially, —$CH(OMe)_2$.

Preferred —Y groups are those having terminal —C≡CH or acetal functionalities:

1. $-(CR^1{}_2)_n-C≡CH$, wherein n is an integer from 1 to about 6;

2.

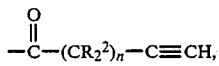

wherein n is an integer from 0 to about 5;
3.

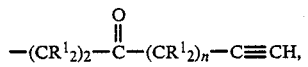

wherein n is an integer from 0 to about 3;
4.

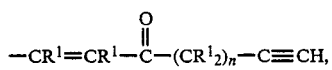

wherein n is 0 or 1;

5. $-(CR^1{}_2)_n-CH(ZR^4)_2$, wherein n is an integer from 1 to about 6;

6.

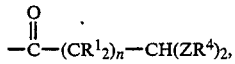

wherein n is an integer from 1 to about 5; and

7.

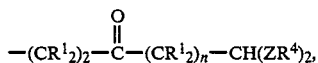

wherein n is an integer from 1 to about 3.
Most preferred Y groups are:
1.

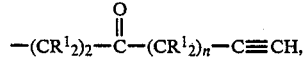

wherein n is an integer from 0 to about 3;
2.

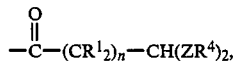

wherein n is an integer from 1 to about 5; and, especially,
3.

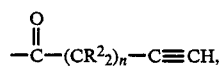

wherein n is an integer from 0 to about 5, more preferred is wherein n is an integer from 1 to about 4; most preferred is n=3.

The compounds of the present invention include their pharmaceutically-acceptable salts. The term "pharmaceutically-acceptable salts", as used herein, means the compounds in their salt form which have the same general pharmacological properties as the protonated form from which they are derived, and which are acceptable from a toxicity viewpoint. Pharmaceutically-acceptable salts include alkali metal (e.g., sodium and potassium), alkaline earth metal (e.g., calcium and magnesium), non-toxic heavy metal (e.g., stannous and indium), and ammonium and low molecular weight substituted ammonium (mono-, di- and tri-methyl or ethyl ammonium) salts. Preferred are the sodium, potassium, and ammonium salts.

The compounds of the present invention may have utility as one or more of the following: anti-inflammatory agents, analgesic agents, antipyretic agents, antiarthritic agents, antiresorptive agents, immunomodulating agents, antilipidemic agents, anti-aging agents or agents for reversing ischaemia-induced cell damage; and are potentially useful for treating one or more of the following diseases or conditions; rheumatoid arthritis, osteoarthritis, bone loss diseases, periodontal disease, gingivitis, allergic rhinitis, asthma, hay fever, shock lug and pulmonary edema, bronchitis and emphysema, signs and symptoms associated with colds and flu, Crohn's disease, inflammatory bowel disease, myocardial infarction (ischemic damage from reperfusion), post-stroke ischemic damage to brain, contact dermatitis, psoriasis, atopic dermatitis, poison ivy, urticaria, allergic eczema, allergic conjuctivitis, atherosclerosis, anaphylactic shock, cerebral stroke damage, gout, organ transplant rejection, tissue trauma and burns, inflammation reactions of the CNS (i.e., multiple sclerosis), sunburn, and high serum cholesterol.

In order to determine and assess pharmacological activity, testing of these compounds in animals is carried out using various assays known to those skilled in the art. Thus, the anti-inflammatory activity of the compounds can be conveniently demonstrated using an assay designed to test the ability of these compounds to antagonize the local edema which is characteristic of the inflammatory response. Examples of such known tests include the rat carrageenan edema test, the oxazolone-induced inflamed mouse ear test, and the arachidonic acid-induced inflamed mouse ear test. Antipyretic activity may be tested using art-known rat models, and analgesic activity may be tested in art-known models such as the acetylcholine model in mice, the Randall-Selitto model in rats, and the hot-plate test in mice or rats. Another useful art-known test is the adjuvant arthritis test which is a useful model for assessing anti-inflammatory or antiarthritic activity and antiresorptive activity in a chronic, rather than acute, model.

These and other appropriate tests for pharmacological activity are disclosed and/or referred to in U.S. Pat. No. 4,130,666, issued Dec. 19, 1978 to Moore; U.S. Pat. No. 4,440,784, issued Apr. 3, 1984 to Katsumi et al.; Japanese Patent Application No. 85/54315, published Mar. 28, 1985 by Katsumi et al.; European Patent Application Publication No. 59,090, published Sept. 1, 1982 by Yamanouchi Pharmaceutical Co., Ltd.; "Prostaglandin and Leukotriene Synthesis in Mouse Ears Inflamed by Arachidonic Acid", *The Journal of Investigative Dermatology*, 84, pp. 253–256 (1985); U.S. Pat. No. 4,431,656, issued Feb. 14, 1984, to Katsumi et al., "Anti-inflammatory Activity of Anti-oxidants", by K. F. Swingle, et al., Chapter 4 of *Anti-inflammatory and Anti-rheumatic Drugs*, Vol. III (K. D. Rainsford, Editor, CRC Press, Inc., 1985); Adamkiewicz et al., *Canad. J. Biochem. Physio.*, 33, 332 (1955); Selye, *Brit. Med. J.*, 2, 1129 (1949); and Winter, *Proc. Exper. Biol. Med.*, 111, 554 (1962); the disclosures of all these patents and articles being incorporated herein by reference.

The compounds of the present invention are prepared from commercially-available materials. Synthesis techniques disclosed for compounds related to the compounds of the present invention can be adapted by a skilled chemist for the preparation of the present compounds; such synthesis techniques are described, for example, in U.S. Pat. Nos. 4,130,666 and 4,440,784, in Japanese Patent Application No. 85/54315, and in copending U.S. patent application No. 879,863 of Loomans, Matthews and Miller, filed June 27, 1986 (U.S. Pat. No. 4,708,966, issues Nov. 24, 1987) all of which are hereby incorporated herein by reference, as well as in several other of the patents and articles incorporated hereinbefore by reference. Representative procedures for synthesizing compounds of the present invention are provided in the Examples hereinafter.

The compounds of the present invention typically comprise from about 0.1% to about 99.9% by weight of the pharmaceutical compositions of the present invention, preferably from about 20% to about 80%, and most preferably from about 40% to about 80%.

As demonstrated by the animal test results provided in the Examples hereinafter, the compounds of the present invention are effective anti-inflammatory agents. Some of the compounds further surprisingly show anti-inflammatory activity at very low dosage levels. In addition, some of the compounds of the present invention are expected to have surprisingly low toxicity, including very little gastrointestinal irritation even when dosed at levels well above dosage levels effective as anti-inflammatory agents. Thus, some of the compounds of the present invention would have very good therapeutic indices. Furthermore, some compounds of the present invention are expected to have prolonged duration of action. This would permit less frequent dosing for the compounds of the present invention relative to the typical dosing every 4–6 hours for most commercially-available anti-inflammatory drugs.

PHARMACEUTICALLY-ACCEPTABLE CARRIER

In addition to the anti-inflammatory agent as described hereinbefore, the pharmaceutical compositions of the present invention essentially contain a pharmaceutically-acceptable carrier. The term "pharmaceutically-acceptable carrier", as used herein, means one or more compatible solid or liquid filler diluents or encapsulating substances which are suitable for administration to a human or lower animal. The term "compatible", as used herein, means that the components of the pharmaceutical composition are capable of being commingled with the anti-inflammatory agent, and with each other, in a manner such that there is no interaction which would substantially reduce the pharmaceutical efficacy of the pharmaceutical composition under ordinary use situations. Pharmaceutically-acceptable carriers must, of course, be of sufficiently high purity and sufficiently low toxicity to render them suitable for administration to the human or lower animal being treated.

Some examples of substances which can serve as pharmaceutically-acceptable carriers are sugars such as lactose, glucose and sucrose; starches such as cornstarch and potato starch; cellulose and its derivatives such as sodium carboxymethylcellulose, ethylcellulose, cellulose acetate; powdered tragacanth; malt; gelatin; talc; stearic acid, magnesium stearate; calcium sulfate; vegetable oils such as peanut oil, cottonseed oil, sesame oil, olive oil, corn oil and oil of theobroma; polyols such as propylene glycol, glycerine, sorbitol, mannitol, and polyethylene glycol; agar; alginic acid; pyrogen-free water; isotonic saline; and phosphate buffer solutions, as well as other non-toxic compatible substances used in pharmaceutical formulations. Wetting agents and lubricants such as sodium lauryl sulfate, as well as coloring agents, flavoring agents, excipients, tableting agents, stabilizers, antioxidants, and preservatives, can also be present. Other compatible pharmaceutical additives and actives (e.g., other NSAI drugs; pain killers; muscle relaxants) may be included in the pharmaceutically-acceptable carrier for use in the compositions of the present invention.

The choice of a pharmaceutically-acceptable carrier to be used in conjunction with the anti-inflammatory agents of the present composition is basically determined by the way the compound is to be administered. If the compound is to be injected, the preferred pharmaceutically-acceptable carrier is sterile, physiologically saline, with blood compatable suspending agent, the pH of which has been adjusted to about 7.4. Suitable pharmaceutically-acceptable carriers for topical application include those suited for use in creams, gels, tapes and the like.

The preferred mode of administering the compounds of the present invention is orally. The preferred unit dosage form is therefore tablets, capsules and the like, comprising a safe and effective amount of the anti-inflammatory compound of the present invention, which is preferably from about 10 mg to about 3500 mg, more preferably from about 25 mg to about 1000 mg, and most preferably from about 25 mg to about 600 mg. Pharmaceutically-acceptable carriers suitable for the preparation of unit dosage forms for oral administration are well-known in the art. Their selection will depend on secondary considerations like taste, cost, shelf stability, which are not critical for the purposes of the present invention, and can be made without difficulty by a person skilled in the art.

The pharmaceutically-acceptable carrier employed in conjunction with the anti-inflammatory agents of the present invention is used at a concentration sufficient to provide a practical size to dosage relationship. The pharmaceutically-acceptable carriers, in total, may comprise from about 0.1% to about 99.9% by weight of the pharmaceutical compositions of the present invention, preferably from about 20% to about 80%, and most preferably from about 20% to about 60%.

METHOD FOR TREATING DISEASES CHARACTERIZED BY INFLAMMATION

Another aspect of the present invention is methods for treating diseases characterized by inflammation. Such methods comprise administering to a human or lower animal in need of such treatment a safe and effective amount of an anti-inflammatory agent described hereinbefore.

The preferred mode of administration is oral, but other known methods of administration are contemplated as well, e.g., dermatomucosally (for example, dermally, rectally and the like) and parenterally (for example, by subcutaneous injection, intra-muscular injection, intra-articular injection, intravenous injection and the like). Ocular administration and inhalation is also included. Thus, specific modes of administration include, without limitation, oral, transdermal, mucosal, sublingual, intranasal, intramuscular, intravenous, intraperitoneal, and subcutaneous administration, as well as topical application.

The term "diseases characterized by inflammation", as used herein, means conditions which are known to involve inflammation, such as arthritis (e.g., rheumatoid arthritis; osteoarthritis; psoriatic arthritis; juvenile arthritis; Reiter's syndrome; infectious arthritis; ankylosing spondylitis; systemic lupus erythematosus; and gout), as well as the presence of inflammation whether or not it is associated with an identifiable disease. Diseases characterized by inflammation further include inflammation of the gastrointestinal tract, including the oral cavity (e.g., inflammation associated with gingivitis or periodontal disease) and bowels (e.g., inflammation associated with Inflammatory Bowel Disease); inflammation associated with dermatological diseases (e.g., psoriasis); and inflammation associated with the respiratory tract (e.g. pulmonary inflammation).

The phrase "safe and effective amount", as used herein, means an amount of a compound or composition high enough to significantly positively modify the condition to be treated, but low enough to avoid serious side effects (at a reasonable benefit/risk ratio), within the scope of sound medical judgment. The safe and effective amount of the anti-inflammatory agent will vary with the particular condition being treated, the age and physical condition of the patient being treated, the severity of the condition, the duration of the treatment, the nature of concurrent therapy, the specific anti-inflammatory agent employed, the particular pharmaceutically-acceptable carrier utilized, and like factor within the knowledge and expertise of the attending physician. However, single dosages can range from about 10 mg to about 3500 mg, or from about 0.2 mg/kg of body weight to about 70 mg/kg of body weight. Preferred single dosages are from about 25 mg to about 600 mg, or from about 0.5 to about 12 mg/kg of body weight. Up to about 6 single dosages per day may be administered.

The following Examples further describe and demonstrate the preferred embodiments within the scope of the present invention. The Examples are given solely for the purpose of illustration, and are not to be construed as limitations of the present invention since many variations thereof are possible without departing from its spirit and scope. All temperature readings are in °C.

Compounds of the present invention can be made according to the scheme shown in the Figure and described hereinbelow. The compound numbers hereinbelow correspond to the numbered compounds in the Figure. —Y is as defined hereinbefore.

EXAMPLE 1

Preparation of 2

To a mixture at 0° C. of 47.5 g (316 mmol) of o-(t-butyl)phenol (1), 91 mL of 40% KOH, and 13 mL of 40% aqueous solution of tetra-n-butylammonium hydroxide (nBu$_4$NOH), a solution of ca. 100 mL of 1,1-dichloro-2,2-difluoroethylene in 250 mL of CH$_2$CL$_2$ is added. The flask is well-stoppered at 0° C. and the mixture is allowed to warm to room temperature and stirred vigorously for 48 hours. The reaction mixture is poured into water and extracted with petroleum ether. The combined organic phase is washed with saturated NaCl and dried (MgSO$_4$). Concentration and short-path distillation gives 83.4 g (93%) of 2: bp 95°/1 torr; IR (film): 2970 (m), 1445 (m), 1310 (s), 1265 (s), 1235 (s), 1175 (s), 1165 (s), 835 (s), 755 (s) cm$^{-1}$; $^1$H-NMR (CDCl$_3$, TMS) δ: 1.40 (s, 9H), 5.95 (t, J=7 Hz, 1H), 7.0–7.5 (m, 4H).

Preparation of 3

A solution of 82.2 g (291 mmol) of 2 in 875 mL of tetrahydrofuran (THF) is treated at −78° C. with 640 mL (1.75 mol) of 2.74M n-butyllithium (nBuLi), keeping the temperature below −60° C. The mixture is stirred at −78° C. for 6 hours and is then allowed to warm very slowly to room temperature, where it is stirred overnight. The reaction is cooled back to −78° C. and to it is added 41.1 g (436 mmol) of methyl disulfide. The solution is allowed to warm to 25° C., stirred for 2 hours, and is then poured into 0.1N HCl. The aqueous portion is extracted with ether and the combined organic phase is washed with saturated NaHCO$_3$ and saturated NaCl, and then dried (MgSO$_4$). GC examination of the reaction mixture reveals a very clean reaction, showing very little else besides 3. The volatile solvents are removed in the hood by distillation, with the pot temperature reaching ca. 110° C. GC analysis at this point shows an ca. 3:1 mixture of 3 and the corresponding thioester derived from hydration of the triple bond. Kugelrohr distillation (oven temp.=110°–140° C., 0.5 torr) affords 43.5 g (ca. 68%) of an approximately 3:1 mixture of 3 and the respective thioester: (Spectra of pure 3) IR (neat): 3480 (m), 2960 (m), 1430 (s), 1225 (m), 745 (s) cm$^{-1}$; $^1$H-NMR (CDCl$_3$, TMS) δ: 1.45 (s, 9H), 2.50 (s, 3H), 6.25 (s, 1H), 6.80 (m, 1H), 7.25 (m, 2H).

Preparation of 4

A mixture of 43.5 g (ca. 193 mmol) of 3 (containing approximately 25% thioester) and 600 mL each of methanol and 3N H$_2$SO$_4$ is refluxed overnight. The reaction solution is concentrated to ca. one-half of its original volume by distilling away the volatiles, and then is cooled to 25° C. and concentrated by means of a water aspirator in the hood (this procedure removes all volatile sulfur-containing by-products). The concentrated reaction is poured into water and extracted with ether. The combined organic phase is washed with saturated NaHCO$_3$ and saturated NaCl, and then dried (MgSO$_4$). The volatiles are removed under reduced pressure and the crude lactone is recrystallized from hexane to afford 23.2 g of pure 4. The mother liquor is flash chromatographed (10% EtOAc/hex) to afford an additional 2.01 g of 4. Total yield of 4 is 25.2 g (69%): mp 99.5°–100° C.; IR (CDCl$_3$): 2965 (s), 1795 (vs), 1430 (s), 1085 (s), 1070 (s) cm$^{-1}$; $^1$H-NMR (CDCl$_3$, TMS) δ: 1.40 (s, 9H), 3.65 (s, 2H), 7.15 (m, 3H); $^{13}$C-NMR (CDCl$_3$, TMS) δ: 29.50, 32.56, 34.19, 122.15, 123.54, 123.90, 125.81, 134.16, 152.65, 174.03.

Preparation of 5

To a solution of 3.80 g (20.0 mmol) of 4 and 5.0 mL (80 mmol) of iodomethane in 100 mL of THF is added portionwise at 0° C. 5.6 g (50 mmol) of potassium t-butoxide (tBuOK). The mixture is stirred at 0° C. for 30 minutes and then is warmed to 25° C. and stirred for an additional 2 hours. The reaction is poured into 0.1N HCl and the aqueous layer is extracted with ether. The combined organic phase is washed with saturated NaHCO$_3$ and saturated NaCl, and then dried (MgSO$_4$). The crude, concentrated reaction mixture is recrystallized from hexane to afford 2.21 g of pure 5. The mother liquid is Kugelrohr distilled (oven temp=160° C., 0.5 torr) to provide an additional 1.19 g of 5 The total yield of 5 is 3.40 g (78%): mp 84°-85° C.; IR (CDCl₃): 2970 (s), 1795 (vs), 1430 (s), 1280 (s), 1055 (s) cm⁻¹; ¹H-NMR (CDCl₃, TMS) δ: 1.40 (s, 9H), 1.50 (s, 6H), 7.15 (m, 3H); ¹³C-NMR (CDCl₃, TMS) δ (off-resonance multiplicity): 25.38 (q), 29.58 (q), 34.21 (s), 42.09 (s), 120.32 (d), 124.14 (d), 125.59 (d), 134.13 (s, two carbons), 150.11 (s), 180.82 (s).

Preparation of 6

A solution of 1.14 g (30.0 mmol) of lithium aluminum hydride (LAH) in 50 mL of ether is treated at 0° C. with 5.45 g (25.0 mmol) of 5. The reaction mixture is warmed to 25° C. and stirred for 1 hour. The excess hydride is decomposed at 0° C. with 25 mL of ethyl acetate followed by 100 mL of a 1:1 mixture of saturated NH₄Cl and water. The reaction mixture is filtered through a short pad of celite, washing it well with ether. The combined organic layer is washed with saturated NaCl and dried (MgSO₄). Concentration leaves the essentially pure 6 in quantitative yield: mp=67°-68° C.; IR (CCl₄): 3640 (m), 3290 (s, br), 2960 (s), 1425 (m), 1385 (m), 1245 (m), 1030 (m) cm⁻¹; ¹H-NMR (CDCl₃, TMS): 1.40 (s, 15H), 1.85 (br s, alcoholic OH, 1H), 3.65 (br s, 2H), 6.6-7.3 (m, 3H), 9.05 (s, phenolic OH, 1H): ¹³C-NMR (CDCl₃, TMS) δ (off-resonance multiplicity): 25.45 (q), 29.99 (q), 34.97 (s), 39.75 (s), 74.13 (t), 118.96 (d), 125.25 (d), 125.58 (d), 133.33 (s), 138.25 (s), 155.28 (s).

Preparation of 7

To a solution of 1.78 g (8.00 mmol) of 6 in 30 mL of dichloromethane is added sequentially at 0° C., 0.68 mL (8.8 mmol) of methanesulfonyl chloride (MsCl) and 2.80 ml (20.0 mmol) of triethylamine (Et₃N). The reaction is stirred for one hour at 0° C. and is poured into saturated NaCl. The aqueous layer is extracted with ether and the combined organic phase is washed with saturated NaCl and dried (MgSO₄). Kugelrohr distillation (oven temp=110° C., 0.5 torr) provides 1.49 g (91%) of 7: IR (neat): 2960 (s), 2870 (m), 1425 (m), 995 (m), 745 (m) cm⁻¹; ¹H-NMR (CDCl₃, TMS) δ: 1.25 (s, 6H), 1.35 (s, 9H), 4.15 (s, 2H), 6.7-7.2 (m, 3H); ¹³C-NMR (CDCl₃, TMS) δ (off-resonance multiplicity): 27.42 (q), 29.36 (q), 34.07 (s), 41.39 (s), 83.57 (t), 119.84 (d), 120.31 (d), 124.58 (d), 133.08 (s), 136.85 (s), 157.11 (s).

Preparation of 9

To a mixture of 2.81 g (12.7 mmol) of 6, 2.37 g (15.8 mmol) of t-butyldimethylchloro silane (tBuMe₂₂SiCl), and 0.38 g (3.2 mmol) of 4-dimethylaminopyridine (DMAP) in 60 mL of dichloromethane is added, at room temperature, 5.23 mL (38.0 mmol) of triethylamine (Et₃N). The reaction mixture is stirred overnight at 25° C. and is then poured into water. The aqueous layer is extracted with ether and the combined organic layer is washed with saturated NaCl and dried (MgSO₄). The crude, concentrated reaction solution is flushed through a short column of silica gel eluting with 2% EtOAc/hex (R_f of 9=0.72) directly into a round-bottomed flask. Concentration affords 4.06 g (95%) of 9; IR (film): 3225 (s, br), 2950 (s), 2930 (s), 1385 (s), 1250 (s), 1050 (s), 835 (s), 780 (s) cm⁻¹; ¹H-NMR (CDCl₃, TMS) δ: 0.15 (s, 6H), 0.95 (s, 9H), 1.45 (s, 15H), 3.70 (s, 2H), 6.6-7.3 (m, 3H), 9.50 (s, 1H).

EXAMPLE 2

Preparation of 8 wherein —Y is

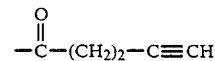

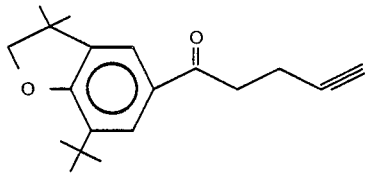

8A

A solution of 1.65 g (8.10 mmol) of 7 in 40 mL of dichloromethane is sequentially treated at −78° C. with 8.90 mmol of 4-pentylnoyl chloride and 1.05 mL (8.90 mmol) of stannic chloride. The mixture is stirred at −78° C. for 1 hour and is then warmed up to ca. −50° C. and is stirred there for 5 minutes. The reaction is then poured into 0.1N HCl and the layers are separated. The aqueous portion is extracted with ether and the combined organic phase is washed with saturated NaHCO₃ and saturated NaCl, and then dried (MgSO₄). Flash chromatography (5% EtOAC/hex) provides a 90% yield of 8A.

EXAMPLE 3

Preparation of 11 wherein —Y is

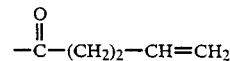

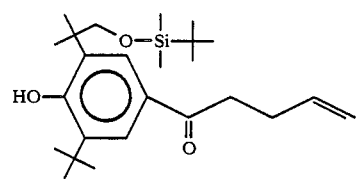

10B

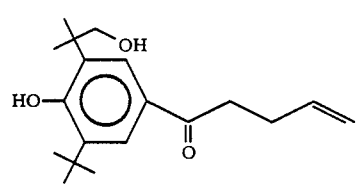

11B

A solution of 9 (3 mmol) in dry CH₂Cl₂ (12 ml) is cooled to −78° C., and 4-pentenoyl chloride (3.3 mmol) [made from the corresponding acid using n-butyllithium (1 equiv., 0° C.-25° C.) followed by oxalyl chloride (1 equiv., 25° C.-40° C.) and used in situ] is added via syringe, followed by SnCl₄ (0.375 ml) added dropwise via syringe, with stirring under argon. After 30 minutes the reaction is allowed to warm to 0° C. and is stirred at that temperature for 5 minutes; it is then quenched with ca. 1 ml of 3N HCl. The reaction is poured into 100 ml water and extracted with 3×50 ml portions of ether. The combined ether layers are washed with 150 ml portions of water until the aqueous layer is neutral (pH test). The ether layer is dried (MgSO4), filtered, and concentrated in vacuo to give crude silylated intermediate 10B. 10B is dissolved in THF (50 ml), and is treated at 25° C. with 6.25 mmol of tetra-n-butylammonium fluoride trihydrate (TBAF). After stirring for one hour, the mixture is poured into saturated NH4Cl and extracted with pentane. The combined organic portion is washed with saturated NaCl, dried over MgSO4, filtered, and concentrated in vacuo. The concentrate is purified by silica gel (sg) chromatography to give pure 11B.

Preparation of 12 wherein —Y is

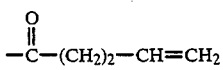

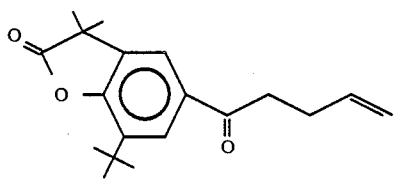
12B

To a solution of 4.75 mmol of 11B in 15 mL of acetone is added at 0° C. 15 mL of Jones reagent (prepared from 6.65 g of sodium dichromate dihydrate and 5 mL of conc. H2SO4, diluted to 15 mL with water). The mixture is stirred at 0° C. for 15 minutes and then stirred overnight at room temperature. The reaction solution is then poured into a mixture of water and ether and the layers are separated. The aqueous portion is extracted with ether and the combined organic phase is washed with saturated NaHCO3 and saturated NaCl, and then dried (MgSO4). Flash chromatography using 10% EtAc/hexane purifies the crude product to give about a 60% yield of 12B.

EXAMPLE 4

Preparation of 13 wherein —Y is

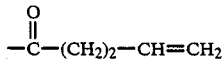

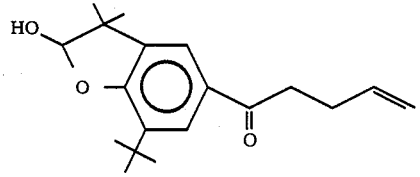
13B

To a solution of 3.30 mmol of 11B in 50 mL of dichloromethane is added at 25° C. 1.36 g (3.63 mmol) of pyridinium dichromate (PDC). The mixture is stirred at room temperature for 8 hours before diluting it with 100 mL of ether and filtering the solid. Concentration followed by flash chromatography (15% EtOAc/hexane) provides yields of about 30% 13B and about 10% 12B along with about 50% recovered 11B.

It is readily understood that a skilled chemist can prepare compounds of the present invention analogous to Compounds 8A, 12B and 13B by using the appropriate raw material Cl-Y and making appropriate adjustments to the exemplary preparations of Examples 3 and 4 hereinabove.

EXAMPLE 5

Carrageenan Rat Paw Edema Test

Male Sprague-Dawley rats (Charles River Laboratories) are weighed and food fasted overnight. The animals are then divided into four to six groups of six animals each according to body weights (average about 145 g) so that each group has about the same average body weight (within 10 g).

The following morning animals are dosed with the test compound and then placed in individual cages. For oral dosing, the drug is suspended in 0.5% methyl cellulose with 2% Tween 80, and delivered via stomach tube in a 5 ml volume.

Paw volumes (0 time) are determined on both hind paws with a mercury displacement device equipped with a transducer and digitizer. One hour after dosing the test compound, the animals are placed in a plastic restrainer and 50 ul of a 1% (w/w) carrageenan solution in 0.9% saline is injected into the ventral surface of the left rear paw. Four hours after the carrageenan injection, the paw volumes are again determined.

The results are expressed as percent inhibition of the mean paw volume of the test group relative to the control group. Statistical differences are determined by one way analysis of variance. $ID_{35}$ values are determined by regression analysis.

TABLE 1

| | Carrageenan Rat Paw Edema Test Results | | | |
|---|---|---|---|---|
| | Compound | | Percent Inhibition at 100 mg/kg | |
| No. | —A— | —Y | dose p.o.* | $ID_{35}$(mg/kg) |
| 8C | —CH2— | O‖<br>—C—(CH2)3—C≡CH | 48.8 | 2.4 |
| 12C | O‖<br>—C— | O‖<br>—C—(CH2)3—C≡CH | 36.1 | N.D. |
| 13C | OH<br>—CH— | O‖<br>—C(CH2)3—C≡CH | 53.2 | 12.9 |

TABLE 1-continued

Carrageenan Rat Paw Edema Test Results

| Compound No. | —A— | —Y | Percent Inhibition at 100 mg/kg dose p.o.* | ID$_{35}$(mg/kg) |
|---|---|---|---|---|
| 8D | —CH$_2$— | —C(=O)—(CH$_2$)$_2$—CH(OH)—C≡CH | 60.8 | 1.6 |

N.D. = Not Determined.
*All values are statistically significant from control at $P \leq 0.05$.

EXAMPLE 6

Pharmaceutical Compositions in Tablet Form

Tablets are prepared by conventional methods, such as mixing and direct compaction, formulated as follows:

| Ingredient | mg per tablet |
|---|---|
| Compound 8C | 200 |
| Microcrystalline cellulose | 100 |
| Sodium starch glycolate | 30 |
| Magnesium stearate | 3 |

When administered orally two times daily, the above composition significantly reduces the inflammation in a patient suffering from rheumatoid arthritis. A significant benefit is also achieved by twice daily administration of this composition to a patient suffering from osteoarthritis.

Similar results are achieved with tablets formulated as above but replacing the 100 mg of Compound 8C with: 500 mg of Compound 13C; or 100 mg of Compound 8D.

EXAMPLE 7

Pharmaceutical Compositions in Capsule Form

Capsules are prepared by conventional methods, comprised as follows:

| Ingredient | mg per capsule |
|---|---|
| Compound 8C | 200 |
| Lactose | To fill to volume of capsule |

The above capsule administered orally once a day substantially reduces the symptomology in a patient afflicted with rheumatoid arthritis or osteoarthritis. Similar results are achieved with capsules formulated a above but replacing Compound 8C with Compounds 8A, 12B, 13B, 12C, 13C, or 8D.

While particular embodiments of the present invention have been described, it will be obvious to those skilled in the art that various changes and modifications to the compounds and compositions disclosed herein can be made without departing from the spirit and scope of the invention. It is intended to cover, in the appended claims, all such modifications that are within the scope of this invention.

What is claimed is:

1. A compound having the structure:

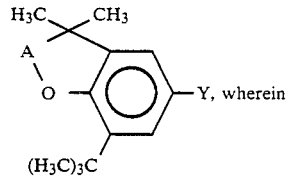

wherein (a) —A— is selected from the group consisting of $$-CH_2-, -\underset{\underset{H}{|}}{CH}-, \text{ and } -\underset{\|}{C}-;$$

(b) —Y is selected from the group consisting of:
(1) —(CR$^1$$_2$)$_n$—C≡C—H, wherein n is an integer from 1 to 6;
(2)

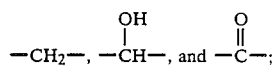

wherein n is an integer from 0 to 5;
(3)

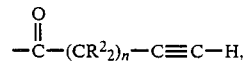

wherein m is an integer from 1 to 5, and m+n is an integer from 1 to 5;
(4)

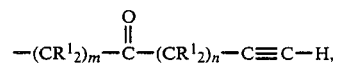

wherein n is 0 or 1;
(5) —(CR$^1$$_2$)$_n$—CR$^3$=CH$_2$, wherein n is an integer from 2 to 6;
(6)

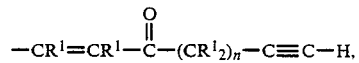

wherein n is an integer from 0 to 5;
(7)

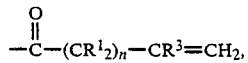

wherein m is an integer from 1 to 3, and m+n is an integer from 1 to 3;
(8)

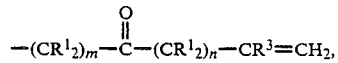

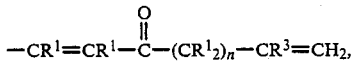

wherein n is an integer from 0 to 3;
(9) $-(CR^1{}_2)_n-CR^3=C=CH_2$, wherein n is an integer from 0 to 6;
(10)

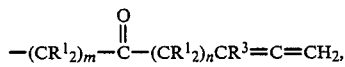

wherein m+n is an integer from 0 to 5;
(11)

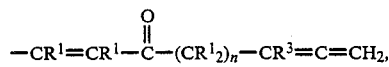

wherein n is an integer from 0 to 3;
(12) $-(CR^1{}_2)_n-CH(ZR^4)_2$, wherein n is an integer from 1 to 6; and
(13)

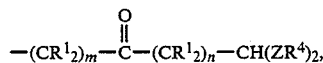

wherein n is an integer from 1 to 5, m is an integer from 0 to 4, and m+n is an integer from 1 to 5;

and wherein each $-R^1$ is independently selected from the group consisting of $-H$, $-OR^3$, $-NR^3{}_2$, $-NR^3{}_3+$, $-N(R^3)C(O)R^3$, $-O_2CR^3$, $-CO_2R^3$, $-C(O)NR^3{}_2$, straight or branched chain saturated alkyl group having from 1 to 3 carbon atoms, and straight or branched chain alkenyl or alkynyl group having from 1 to 3 carbon atoms, or two $-R^1$'s on the same carbon atom are $=O$ or $=CR^3{}_2$; each $-R^2$ is independently selected from the group consisting of $-H$, $-OR^3$, $-NR^3{}_2$, $-NR^3{}_3+$, $-N(R^3)C(O)R^3$, $-O_2CR^3$, $-CO_2R^3$, $-C(O)NR^3{}_2$, straight or branched chain saturated alkyl group having from 1 to 3 carbon atoms, and alkenyl or alkynyl group having from 1 to 2 carbon atoms, or two $-R^2$'s on the same carbon atom are $=O$ or $=CR^3{}_2$; each $-R^3$ is independently selected from the group consisting of $-H$, methyl and ethyl; each $-R^4$ is independently selected from the group consisting of $-CH_3$ and $-CH_2CH_3$, or the $-R^4$'s may be joined to form a cyclic acetal such that both $-R^4$'s together are one group selected from $-(CH_2)_2-$ and $-(CH_2)_3-$; and each $-Z-$ is independently selected from the group consisting of $-O-$, $-S-$, $-NH-$, and $-NR^4-$; or the pharmaceutically-acceptable salt thereof.

2. The compound of claim 1 wherein $-A-$ is

3. The compound of claim 1 wherein $-A-$ is $-CH_2-$.
4. The compound of claim 1 wherein:
(a) each $-R^1$ and $-R^2$ is independently selected from the group consisting of $-H$, $-OH$, methyl, ethyl, or two $-R^1$'s or $-R^2$'s on the same carbon atom are $=O$ or $=CH_2$; and wherein further no more than about two $-R^1$ or $-R^2$ groups are a group other than $-H$;
(b) each $-R^3$ is $-H$;
(c) each $-R^4$ is methyl or both $-R^4$ groups together are the group $-(CH_2)_2-$ which forms a cyclic acetal; and
(d) each $-Z-$ is independently selected from the group consisting of $-O-$ or $-S-$.

5. The compound of claim 4 wherein the $-Y$ group is selected from the group consisting of:
(1) $-(CR^1{}_2)_n-C\equiv CH$, wherein n is an integer from 1 to 6;
(2)

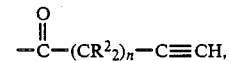

wherein n is an integer from 0 to 5;
(3)

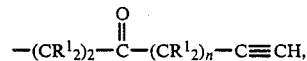

wherein n is an integer from 0 to 3;
(4)

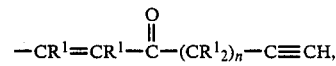

wherein n is 0 or 1;
(5) $-(CR^1{}_2)_n-CH(ZR^4)_2$, wherein n is an integer from 1 to 6;
(6)

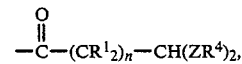

wherein n is an integer from 1 to 5; and
(7)

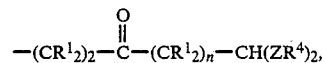

wherein n is an integer from 1 to 3.

6. The compound of claim 5 wherein the $-Y$ group is selected from the group consisting of
(1)

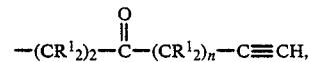

wherein n is an integer from 0 to 3;
(2)

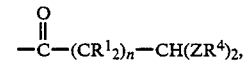

wherein n is an integer from 1 to 5; and,
(3)

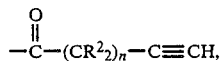

wherein n is an integer from 0 to 5.

7. The compound of claim 6 wherein —A— is —CH$_2$—.

8. The compound of claim 6 wherein each —R$^1$ and —R$^2$ is —H, and each —Z— is —O—.

9. The compound of claim 7 wherein —Y is

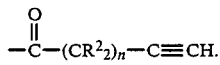

10. The compound of claim 9 wherein n is 3 and each —R$^2$ is —H.

11. The compound of claim 7 wherein —Y is

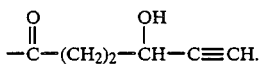

12. A pharmaceutical composition comprising:
(a) a safe and effective amount of an anti-inflammatory compound according to claim 1; and
(b) a pharmaceutically-acceptable carrier.

13. A pharmaceutical composition comprising:
(a) a safe and effective amount of an anti-inflammatory compound according to claim 4; and
(b) a pharmaceutically-acceptable carrier.

14. A pharmaceutical composition comprising:
(a) a safe and effective amount of an anti-inflammatory compound according to claim 6; and
(b) a pharmaceutically-acceptable carrier.

15. A pharmaceutical composition comprising:
(a) a safe and effective amount of an anti-inflammatory compound according to claim 9; and
(b) a pharmaceutically-acceptable carrier.

16. A method for treating diseases characterized by inflammation, said method comprising administering to a human or lower animal in need of such treatment a safe and effective amount of an anti-inflammatory compound of claim 1.

17. A method for treating diseases characterized by inflammation, said method comprising administering to a human or lower animal in need of such treatment a safe and effective amount of an anti-inflammatory compound of claim 4.

18. A method for treating diseases characterized by inflammation, said method comprising administering to a human or lower animal in need of such treatment a safe and effective amount of an anti-inflammatory compound of claim 6.

19. A method for treating diseases characterized by inflammation, said method comprising administering to a human or lower animal in need of such treatment a safe and effective amount of an anti-inflammatory compound of claim 9.

* * * * *

UNITED STATES PATENT AND TRADEMARK OFFICE
CERTIFICATE OF CORRECTION

PATENT NO. : 4,849,428
DATED : July 18, 1989
INVENTOR(S) : R.L.M. Dobson, M.E. Loomans, R.S. Matthews and J.A. Miller It is certified that error appears in the above-identified patent and that said Letters Patent is hereby corrected as shown below:

Column 4, lines 58-60, "$-\overset{O}{\overset{\|}{C}}-(CR^2{}_2)_n-C\equiv CH,$" should be -- $-CH{\overset{\displaystyle -O-}{\underset{\displaystyle -O-}{\big<}}}\Big],$ --.

Column 5, lines 1-4, "$-\overset{O}{\overset{\|}{C}}(CR_2{}^2)_n-C\equiv CH,$" should be -- $-\overset{O}{\overset{\|}{C}}-(CR^2{}_2)_n-C\equiv CH,$ --.

Column 6, line 14, "lug" should be --lung--.

Column 8, lines 18-19, "physiologically" should be --physiological--.

Column 9, line 59, "$CH_2CL_2$" should be --$CH_2Cl_2$--.

Column 11, line 52, "$(tBuMe_{22}SiCl)$" should be --$(tBuMe_2SiCl)$--.

Column 14, lines 61-62, "$-\overset{O}{C}-$" should be -- $-\overset{O}{\overset{\|}{C}}-$ --.

Column 14, lines 65-66, "$-\overset{OH}{CH}-$" should be -- $-\overset{OH}{\overset{|}{CH}}-$ --.

Column 15, line 56, "a" should be --as--.

Signed and Sealed this

Twenty-fifth Day of September, 1990

Attest:

HARRY F. MANBECK, JR.

*Attesting Officer*   *Commissioner of Patents and Trademarks*